United States Patent
Song et al.

(10) Patent No.: US 11,574,112 B2
(45) Date of Patent: *Feb. 7, 2023

(54) SYSTEM AND METHOD FOR GENERATING AND EDITING DIAGNOSIS REPORTS BASED ON MEDICAL IMAGES

(71) Applicant: Keya Medical Technology Co., Ltd., Beijing (CN)

(72) Inventors: Qi Song, Seattle, WA (US); Feng Gao, Seattle, WA (US); Hanbo Chen, Seattle, WA (US); Shanhui Sun, Princeton, NJ (US); Junjie Bai, Seattle, WA (US); Zheng Te, Beijing (CN); Youbing Yin, Kenmore, WA (US)

(73) Assignee: KEYA MEDICAL TECHNOLOGY CO., LTD., Beijing (CN)

( * ) Notice: Subject to any disclaimer, the term of this patent is extended or adjusted under 35 U.S.C. 154(b) by 43 days.

This patent is subject to a terminal disclaimer.

(21) Appl. No.: 17/017,657

(22) Filed: Sep. 10, 2020

(65) Prior Publication Data

US 2020/0410678 A1 Dec. 31, 2020

Related U.S. Application Data

(63) Continuation of application No. 16/179,952, filed on Nov. 4, 2018, now Pat. No. 10,803,581, which is a
(Continued)

(51) Int. Cl.
*G06V 10/00* (2022.01)
*G06F 40/10* (2020.01)
(Continued)

(52) U.S. Cl.
CPC .............. *G06F 40/10* (2020.01); *G06F 16/50* (2019.01); *G06F 40/174* (2020.01);
(Continued)

(58) Field of Classification Search
CPC ......... G06K 9/80; G06T 7/0012; G06F 16/50; G06F 17/30244; G06F 40/10;
(Continued)

(56) References Cited

U.S. PATENT DOCUMENTS 5,807,256 A * 9/1998 Taguchi ................. G16H 50/20
600/425
7,261,691 B1 8/2007 Asomani
(Continued)

FOREIGN PATENT DOCUMENTS

CN 106569673 A 4/2017
CN 106780460 A 5/2017
(Continued)

OTHER PUBLICATIONS

Simonyan, K. et al., "Very Deep Convolutional Networks for Large-Scale Image Recognition", arXiv:1409.1556v6 [cs.CV] Apr. 10, 2015; 14 pages.
(Continued)

*Primary Examiner* — Amir Alavi
(74) *Attorney, Agent, or Firm* — Bayes PLLC

(57) ABSTRACT

Embodiments of the disclosure provide systems and methods for generating a report based on a medical image of a patient. An exemplary system includes a communication interface configured to receive the medical image acquired by an image acquisition device. The system may further include at least one processor. The at least one processor is configured to automatically determine keywords from a natural language description of the medical image generated by applying a learning network to the medical image. The at least one processor is further configured to generate the report describing the medical image of the patient based on the keywords. The at least one processor is also configured to provide the report for display.

20 Claims, 7 Drawing Sheets

Related U.S. Application Data continuation-in-part of application No. 16/154,681, filed on Oct. 8, 2018, now Pat. No. 10,803,579.

(60) Provisional application No. 62/582,092, filed on Nov. 6, 2017.

(51) Int. Cl.

| | | |
|---|---|---|
| *G06T 7/00* | (2017.01) | |
| *G06N 3/04* | (2006.01) | |
| *G06N 3/08* | (2006.01) | |
| *G06F 16/50* | (2019.01) | |
| *G06F 40/174* | (2020.01) | |
| *G06V 10/20* | (2022.01) | |
| *G06N 20/00* | (2019.01) | |

(52) U.S. Cl.
CPC ......... *G06N 3/0445* (2013.01); *G06N 3/0454* (2013.01); *G06N 3/08* (2013.01); *G06T 7/0012* (2013.01); *G06V 10/20* (2022.01); *G06N 3/0472* (2013.01); *G06N 20/00* (2019.01)

(58) Field of Classification Search
CPC .. G06F 40/174; G06N 99/005; G06N 3/0445; G06N 3/0454; G06N 3/08; G06N 3/0472
See application file for complete search history.

(56) References Cited

U.S. PATENT DOCUMENTS

| | | | |
|---|---|---|---|
| 7,302,164 B2 | 11/2007 | Wright et al. | |
| 7,346,203 B2 | 3/2008 | Turek et al. | |
| 7,693,317 B2* | 4/2010 | Vining | G16H 30/40 382/128 |
| 7,711,583 B2 | 5/2010 | Epstein et al. | |
| 7,894,676 B2* | 2/2011 | Iizuka | G16H 50/70 382/209 |
| 8,312,057 B2* | 11/2012 | John | G10L 17/00 707/804 |
| 8,401,260 B2 | 3/2013 | Nirmal et al. | |
| 8,423,571 B2* | 4/2013 | Moriya | G16H 15/00 707/769 |
| 8,612,258 B2* | 12/2013 | Moitra | G16H 30/20 705/3 |
| 9,390,236 B2* | 7/2016 | Geller | G16H 30/20 |
| 9,594,878 B2 | 3/2017 | Silva et al. | |
| 9,788,799 B2* | 10/2017 | Wagner | A61B 90/50 |
| 9,824,457 B2 | 11/2017 | Wenzel et al. | |
| 9,846,938 B2 | 12/2017 | Steigauf et al. | |
| 9,959,386 B2 | 5/2018 | Ohad et al. | |
| 10,002,311 B1* | 6/2018 | Garnavi | G06N 3/0454 |
| 10,248,759 B2 | 4/2019 | Larcom et al. | |
| 10,262,107 B1* | 4/2019 | Tran | G06F 19/3475 |
| 10,347,378 B2* | 7/2019 | Okabe | G16H 40/63 |
| 10,395,420 B2 | 8/2019 | Vilsmeier | |
| 10,553,312 B2* | 2/2020 | Bernard | A61B 6/032 |
| 10,579,234 B2 | 3/2020 | Reichter | |
| 10,803,581 B2* | 10/2020 | Song | G06T 7/0012 |
| 2006/0242143 A1* | 10/2006 | Esham | G16H 15/00 |
| 2006/0284732 A1 | 12/2006 | Brock-Fisher | |
| 2009/0171225 A1* | 7/2009 | Gadodia | G16H 15/00 600/508 |
| 2012/0059664 A1 | 3/2012 | Georgiev et al. | |
| 2015/0112722 A1 | 4/2015 | Dees et al. | |
| 2017/0098153 A1 | 4/2017 | Mao et al. | |
| 2017/0132526 A1 | 5/2017 | Cohen et al. | |
| 2017/0337329 A1* | 11/2017 | Liu | A61B 6/463 |
| 2018/0373985 A1* | 12/2018 | Yang | G06V 20/41 |
| 2019/0114766 A1 | 4/2019 | Song et al. | |
| 2019/0139218 A1 | 5/2019 | Song et al. | |
| 2019/0313903 A1 | 10/2019 | McKinnon | |
| 2020/0020449 A1 | 1/2020 | Brazil | |

FOREIGN PATENT DOCUMENTS

| | | |
|---|---|---|
| CN | 107145910 A | 9/2017 |
| CN | 108665055 A | 10/2018 |

OTHER PUBLICATIONS

Huang, Gao et al., "Densely Connected Convolutional Networks", Proceedings of IEEE Conference on Computer Vision and Pattern Recognition. 2017; 9 pages.

Hochreiter, Sepp et al. "Long Short-Term Memory", Neural Computation, 9(8): pp. 1735-1780, 1997.

Cho, Kyunghyun et al., "On the Properties of Neural Machine Translation: Encoder-Decoder Approaches", arXiv: 1409.1259v2 [cs.CL] Oct. 7, 2014, 9 pages.

First Office action issued in related Chinese Application No. 201811190189.X, dated Apr. 17, 2020, 10 pages.

First Office Action issued in related Chinese Application No. 201811308886.0, dated Aug. 10, 2020, 9 pages.

* cited by examiner

SYSTEM AND METHOD FOR GENERATING AND EDITING DIAGNOSIS REPORTS BASED ON MEDICAL IMAGES

CROSS REFERENCE TO RELATED APPLICATION

This application is a continuation of U.S. application Ser. No. 16/179,952, filed Nov. 4, 2018, which claims the benefits of priority to U.S. Provisional Application No. 62/582,092, filed Nov. 6, 2017, and is a continuation-in-part of U.S. application Ser. No. 16/154,681, filed Oct. 8, 2018, both of which are incorporated herein by reference in their entirety.

TECHNICAL FIELD

The present disclosure relates to a diagnosis report system, and more particularly, to a diagnosis report system that generates a medical diagnosis report based on a user selection of view(s) and/or region(s) of interest of a medical image, generates keywords describing the medical images, and creates a diagnosis report according to a user selection of keywords.

BACKGROUND

Radiologists read medical images to observe abnormalities and make diagnosis of diseases. Writing diagnosis report is also part of routine jobs for radiologists/clinicians. For example, medical diagnosis reports describe and summarize important findings in medical images such as X-ray images, Computed Tomography (CT) images, Magnetic Resonance Imaging (MRI) images, ultrasound images and the like. Medical diagnosis reports of a patient are typically considered to be a very important component of the patient's medical profile. However, currently available processes for generating medical diagnosis reports are inefficient.

Specifically, currently available processes for generating medical diagnosis reports are time-consuming mainly due to two reasons. First, the currently available processes require careful manual visual inspection of one or more medical images of a patient before any findings can be recorded. The medical images may be very large compared to sparsely-located lesions, so the search for suspicious regions can take a significant amount of time. Second, the findings and preliminary conclusions may need to be manually structured into reports, which can only be written or audio-recorded (dictated) by authorized medical professionals such as radiologists or clinicians.

Embodiments of the disclosure address the above problems by providing a diagnosis report system that can automatically analyze medical images, detect suspicious regions, and generate diagnosis reports.

SUMMARY

Embodiments of the disclosure provide a system for generating a report based on a medical image of a patient. The system includes a communication interface configured to receive the medical image acquired by an image acquisition device. The system further includes at least one processor. The at least one processor is configured to automatically determine keywords from a natural language description of the medical image generated by applying a learning network to the medical image. The at least one processor is further configured to generate the report describing the medical image of the patient based on the keywords. The at least one processor is also configured to provide the report for display.

Embodiments of the disclosure also provide a method for generating a report based on a medical image of a patient. The method includes receiving the medical image, by a communication interface. The medical image is acquired by an image acquisition device. The method further includes automatically determining keywords, by at least one processor, from a natural language description of the medical image generated by applying a learning network to the medical image. The method also includes generating the report, by the at least one processor, describing the medical image of the patient based on the keywords. The method additionally includes providing the report for display.

Embodiments of the disclosure further provide a non-transitory computer-readable medium having instructions stored thereon that, when executed by one or more processors, cause the one or more processors to perform a method for generating a report based on a medical image of a patient. The method includes receiving the medical image acquired by an image acquisition device. The method further includes automatically determining keywords from a natural language description of the medical image generated by applying a learning network to the medical image. The method also includes generating the report describing the medical image of the patient based on the keywords. The method additionally includes providing the report for display.

It is to be understood that both the foregoing general description and the following detailed description are exemplary and explanatory only and are not restrictive of the invention, as claimed.

DETAILED DESCRIPTION

Figure 1:
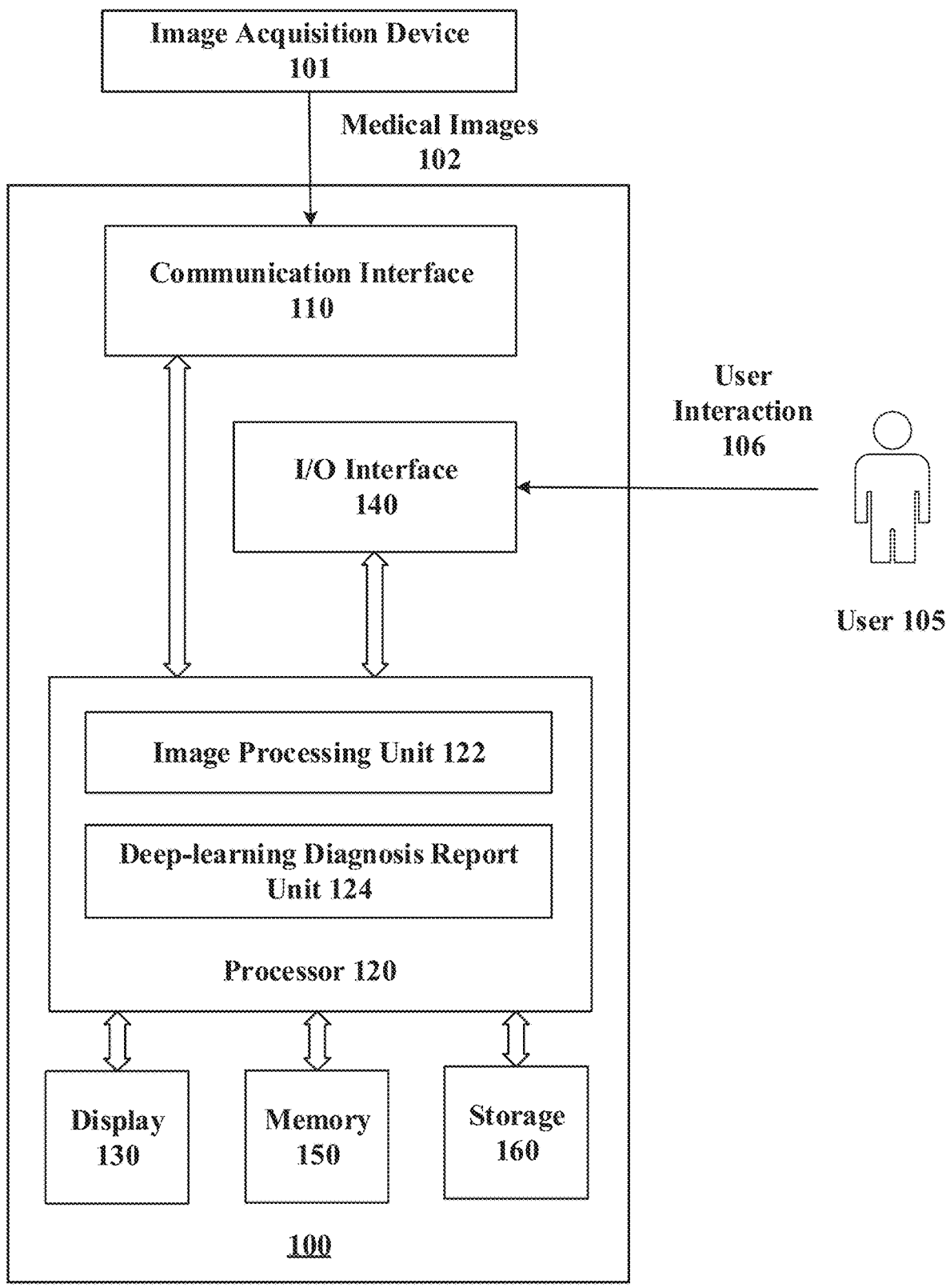
FIG. 1 illustrates a block diagram of an exemplary diagnosis report generating system, according to embodiments of the disclosure.

Reference will now be made in detail to the exemplary embodiments, examples of which are illustrated in the accompanying drawings. Wherever possible, the same reference numbers will be used throughout the drawings to refer to the same or like parts.

Embodiments of the present disclosure provide automated analysis of medical images and generation of medical diagnosis reports. Specifically, a system configured in accordance with embodiments of the present disclosure may automatically analyze medical images, detect suspicious regions, and generate diagnosis reports. In some embodiments, the system may be supported by deep-learning-based image processing and natural language processing backend processes. In some embodiments, medical professionals (e.g., radiologists, clinicians, or doctors) using the system may edit/correct the algorithm-generated diagnosis report and may add new findings via an interactive user interface. A radiologist/clinician may, for example, manually type or dictate edits/corrections through the interactive user interface. A doctor may, for example, filter a desired sentence in the generated report by selecting one or more medical keywords from the generated reports. In some embodiments, a system configured in accordance with embodiments of the present disclosure may support the generation of descriptions at a finer scale in addition to providing whole-image-based diagnosis reports. For example, a user may select one or more regions of interest in one or more medical images and the system may automatically generate a diagnosis description according to the selected region(s) of interest. It is contemplated that systems and methods disclosed in the present disclosure can significantly reduce the amount of time medical professionals need to spend on each patient and can help improve the efficiency in diagnosis of diseases.

In some embodiments, a system configured in accordance with embodiments of the present disclosure may support automatic or semi-automatic generation of medical reports for both whole image(s) (or multiple images of the same patient), and/or specific region(s) of interest. The reports may include descriptions of clinical observations. The reports may also include images related to the observations.

In some embodiments, a system configured in accordance with embodiments of the present disclosure may generate and display keywords of the descriptions of the clinical observations. The system may provide an interface that allows users to select contents to be reported by selecting the keywords.

In some embodiments, the descriptions and the keywords can be interactively generated based on the image the user selected for viewing. For instance, if a user chooses to tile all images for viewing, then the system may generate a description of the overall impression of the images. On the other hand, if the user chooses to view a slice of a three-dimensional (3D) image, then the system may generate a description of that particular slice. If the user chooses to zoom-in and view an enlarged part of an image slice, then the system may generate a description of the enlarged part accordingly.

In some embodiments, the descriptions and the keywords can be interactively generated by combining annotation information available to the system. For instance, a user can annotate on an image and the system may include the annotation information when generating the descriptions and the keywords.

In some embodiments, the descriptions and the keywords can be interactively generated by combining speech information available to the system. For instance, a user can choose to record a speech (e.g., describing an image or part(s) of the image) and the system may include the speech information when generating the descriptions and the keywords.

In some embodiments, a system configured in accordance with embodiments of the present disclosure may automatically detect whether the recorded speech is a complete description (e.g., not merely a set of keywords). If the speech is determined to be a complete description, the system may convert the speech to text (e.g., utilizing one or more speech recognition techniques) and add the converted text to the report(s).

In some embodiments, the descriptions and the keywords can be interactively generated by combining text information available to the system. For instance, a user can type in keywords or sentences as text information and the system may include the text information when generating the description and the keywords.

In some embodiments, a system configured in accordance with embodiments of the present disclosure may be supported by an end (e.g., medical image)-to-end (e.g., diagnosis report) deep learning model background process. The end-to-end deep learning model background process may be configured to combine an image processing convolutional neural network (CNN), a natural language processing recurrent neural network (RNN), and an attention process.

In some embodiments, a system configured in accordance with embodiments of the present disclosure may allow a user to add related images to the system when the user adds descriptions to the reports.

In some embodiments, an interactive system configured in accordance with embodiments of the present disclosure may significantly reduce the amount of time and workload of radiologists/clinicians compared with those involved in the traditional image inspection/diagnosis report writing procedure.

FIG. 1 illustrates a block diagram of an exemplary diagnosis report generating system 100, according to embodiments of the disclosure. Consistent with the present disclosure, diagnosis report generating system 100 may be configured to generate a diagnosis report based on medical images 102 acquired by an image acquisition device 101. Consistent with the present disclosure, diagnosis report generating system 100 may receive medical images 102 from image acquisition device 101. Alternatively, medical images 102 may be stored in an image database (not shown) and diagnosis report generating system 100 may receive medical images 102 from the image database. In some embodiments, medical images 102 may be two-dimensional (2D) or three-dimensional (3D) images. A 3D image may contain multiple 2D image slices. In some embodiments, medical images 102 may contain images in a tile view or various cross-sectional views, e.g., sagittal, coronal, and transverse views.

In some embodiments, image acquisition device 101 may acquire medical images 102 using any suitable imaging modalities, including, e.g., functional MRI (e.g., fMRI, DCE-MRI and diffusion MRI), Cone Beam CT (CBCT), Spiral CT, Positron Emission Tomography (PET), Single-Photon Emission Computed Tomography (SPECT), X-ray, optical tomography, fluorescence imaging, ultrasound imaging, and radiotherapy portal imaging, etc.

For example, image acquisition device 101 may be an MRI scanner. The MRI scanner includes a magnet that surrounds a patient tube with a magnetic field. A patient is positioned on a padded table that can move into the patient tube. The MRI scanner further includes gradient coils in multiple directions (e.g., x, y, and z directions) to create a spatially varying magnetic field on top of a uniform magnetic field created by the magnet. The uniform magnetic field used by the MRI scanner are typically between 0.2 T-7 T, e.g., around 1.5 T or 3T. The MRI scanner also includes RF coils to excite the tissues inside the patient body and transceivers to receive electromagnetic signals generated by the tissues while returning to an equilibrium state.

As another example, image acquisition device 101 may be a CT scanner. The CT scanner includes an X-ray source that emits X-rays against body tissues and a receiver that receives the residual X-rays after attenuated by the body tissues. The CT scanner also includes rotating mechanism to capture X-ray images at different view angles. Such rotating mechanism can be a rotating table that rotates the patient, or a rotating structure that rotates the X-ray source and the receiver around the patient. The X-ray images at different angles are then processed by a computer system to construct a two-dimensional (2D) cross section image or a three-dimensional (3D) volume image.

In some embodiments, as shown in FIG. 1, diagnosis report generating system 100 may include a communication interface 110, a processor 120, a display 130, an I/O interface 140, a memory 150, and a storage 160. In some embodiments, diagnosis report generating system 100 may have different modules in a single device, such as an integrated circuit (IC) chip (implemented as an application-specific integrated circuit (ASIC) or a field-programmable gate array (FPGA)), or separate devices with dedicated functions. In some embodiments, one or more components of diagnosis report generating system 100 may be allocated in a cloud computing environment, or may be alternatively or additionally in a single location (such as in a computer inside or close to a radiologist's office) or distributed locations. Components of diagnosis report generating system 100 may be in an integrated device, or distributed among different devices but in communication with each other through a network (not shown) or one or more direct communication links.

Communication interface 110 may send data to and receive data from external systems or devices, such as image acquisition device 101, via communication cables, a Wireless Local Area Network (WLAN), a Wide Area Network (WAN), wireless networks such as via radio waves, a cellular or telecommunication network, and/or a local or short-range wireless network (e.g., Bluetooth™), or other communication methods. In some embodiments, communication interface 110 may include an integrated services digital network (ISDN) card, cable modem, satellite modem, or a modem to provide a data communication connection. As another example, communication interface 110 may include a local area network (LAN) card (e.g., Ethernet adapter) to provide a data communication connection to a compatible LAN. Wireless links can also be implemented by communication interface 110. In such an implementation, communication interface 110 can send and receive electrical, electromagnetic, and/or optical signals that carry analog/digital data streams representing various types of information via a network or direct communication link(s).

Consistent with some embodiments, communication interface 110 may receive medical images 102 acquired by image acquisition system 101. Communication interface 110 may further provide the received medical images 102 to memory 150 and/or storage 160 for storage or to processor 120 for processing.

Processor 120 may include any appropriate type of general-purpose or special-purpose microprocessor, digital signal processor, or microcontroller. Processor 120 may be configured as a stand-alone processor module dedicated to diagnosis report generation. Alternatively, processor 120 may be configured as a shared processor module for performing other functions unrelated to diagnosis report generation.

As shown in FIG. 1, processor 120 may include multiple modules (also referred to as units), such as an image processing unit 122, a deep-learning diagnosis report unit 124, and the like. These modules (and any corresponding sub-modules or sub-units) may be hardware units (e.g., portions of an integrated circuit) of processor 120 designed for use with other components or software units implemented by processor 120 through executing at least part of a program. The program may be stored on a computer-readable medium (e.g., memory 150, storage 160, or an external storage unit), and when executed by processor 120, it may perform one or more functions or operations.

Although FIG. 1 shows units 122 and 124 both within one processor 120, it is contemplated that these units may be distributed among multiple processors located near or remotely with respect to each other.

Image processing unit 122 may be configured to process medical images 102 received through communication interface 110. In some embodiments, image processing unit 122 may perform pre-processing on medical images 102, such as filtering to reduce image artifacts or noises, and leveling image quality, e.g., by adjusting the images' exposure parameters to increase contrast. In some embodiments, pre-processing may also include resizing or normalization of medical images 102. Such pre-processing may condition medical images 102 before they are displayed on a user interface (e.g., on display 130). In some embodiments, image processing unit 122 may also perform computer-aided diagnosis functions, such as to identify conspicuous structures related to possible diseases.

Deep-learning diagnosis report unit 124 may be configured to perform report generation algorithms to generate a diagnosis report based on the output of image processing unit 122. In some embodiments, the diagnosis report may include various patient, examination, and diagnosis information. In some embodiments, the diagnosis report may be automatically or semi-automatically generated by deep-learning generation unit 124. In some embodiments, deep-learning generation unit 124 may generate the diagnosis report interactively with input from a user 105, e.g., a radiologist, through use of I/O interface 140 that will be described in greater detail later.

In some embodiments, deep-leaning diagnosis report unit 124 may generate diagnosis content of the report using one or more deep-learning methods. Deep-learning generation unit 124 may infer text information of the report from medical images 102.

In some embodiments, deep-learning diagnosis report unit 124 may apply an end-to-end learning network to infer the text information from medical images 102. The end-to-end learning network may include two parts: a first part that extracts image features from medical images 102, and a second part that determines diagnosis descriptions and keywords using the image features. In some embodiments, the first part of the end-to-end learning network may include a convolutional neural network (CNN). In some embodiments, the second part of the end-to-end learning network may include a recursive neural network (RNN). The RNN may generate a natural language description of at least one medical image based on the image features. In some embodiments, the RNN may further determine keywords from the natural language description and provide the keywords to a user for selection. The text included in the report may be generated based on the user selected keywords.

In some embodiments, the end-to-end learning network may include an attention layer in between the CNN and RNN that assigns weights to the image features in different regions of the images. The assigned weights may be different depending on various factors. The CNN, the RNN, and the attention layer may be trained jointly to enhance the performance of the end-to-end learning network. For example, a joint loss function may be used to account for the combined performance of the CNN, the RNN, and the attention layer.

In some embodiments, deep-learning diagnosis report unit 124 may also analyze meta data contained in the patient information in generating the report. The meta data may be recorded through patient registration or generated with medical images 102. For example, the meta data may include age and gender of a patient, patient medical history, and family medical history, etc. For example, the end-to-end learning network may be trained to interpret medical images 102 in light of the patient information. For instance, different image features may be extracted for an image of a pediatric patient as opposed to an image of a senior patient. In another example, diagnosis of lung cancer may change based on a patient's smoking history.

In some embodiments, deep-learning diagnosis report unit 124 may model and construct a diagnosis report. The report may include text information that indicates, among other things, the type of the detected object (e.g., an intra cranial hemorrhage), and the position of the detected object (e.g., left frontal lobe). In some embodiments, the text information may further indicate results of quantitative analysis, such as diameters, volumes, and density distribution, etc. For example, the report may indicate that the size and shape of the object (e.g., 2.6×2.3 cm sphere shape). The report may further include other findings that deep-learning diagnosis report unit 124 is configured to infer from medical images 102, such as if any bone fracture can be observed, or that whether a detected object is likely benign or malignant. In some embodiments, the report may include screenshots of 2D/3D images.

Processor 120 may render visualizations of user interfaces on display 130. Display 130 may include a Liquid Crystal Display (LCD), a Light Emitting Diode Display (LED), a plasma display, or any other type of display, and provide a Graphical User Interface (GUI) presented on the display for user input and data depiction. Display 130 may include a number of different types of materials, such as plastic or glass, and may be touch-sensitive to receive commands from the user. For example, the display may include a touch-sensitive material that is substantially rigid, such as Gorilla Glass™, or substantially pliable, such as Willow Glass™.

The user interfaces may depict data such as medical images 102 and the diagnosis report generated by deep-learning generation unit 124. In some embodiments, medical images 102 and the diagnosis report may be displayed side-by-side. For example, FIGS. 2A-2D illustrate exemplary user interfaces 200 of diagnosis report generating system 100 shown in FIG. 1, according to embodiments of the disclosure. In the exemplary user interfaces 200, images 213 are displayed on the right-hand side and diagnosis report 231 is displayed on the left-hand side. As shown in FIGS. 2A-2D, user interfaces 200 may further include a task bar 201, a view selection bar 210, an image edit tool bar 211, a user input area 220, and a report edit tool bar 230. However, it is contemplated that the relative positions and configurations of the views are exemplary only, and may be re-arranged in other embodiments.

In some embodiments, diagnosis report generating system 100 may provide interactive tools in the user interfaces displayed on display 130, to allow user 105 (e.g., a radiologist/clinician) to edit the medical images and/or the diagnosis report. Returning to FIG. 1, in some embodiments, user 105 may provide a user interaction 106 via I/O interface 140. I/O interface 140 may be an input/output device that is configured to receive user input or provide system output to the user. For example, I/O interface 140 may include a keyboard, a mouse, a click button, a dial wheel, a stylus, a touch-screen, a microphone, a printer, a virtual reality (VR) goggle/controller, or any combination thereof.

Figure 2A:
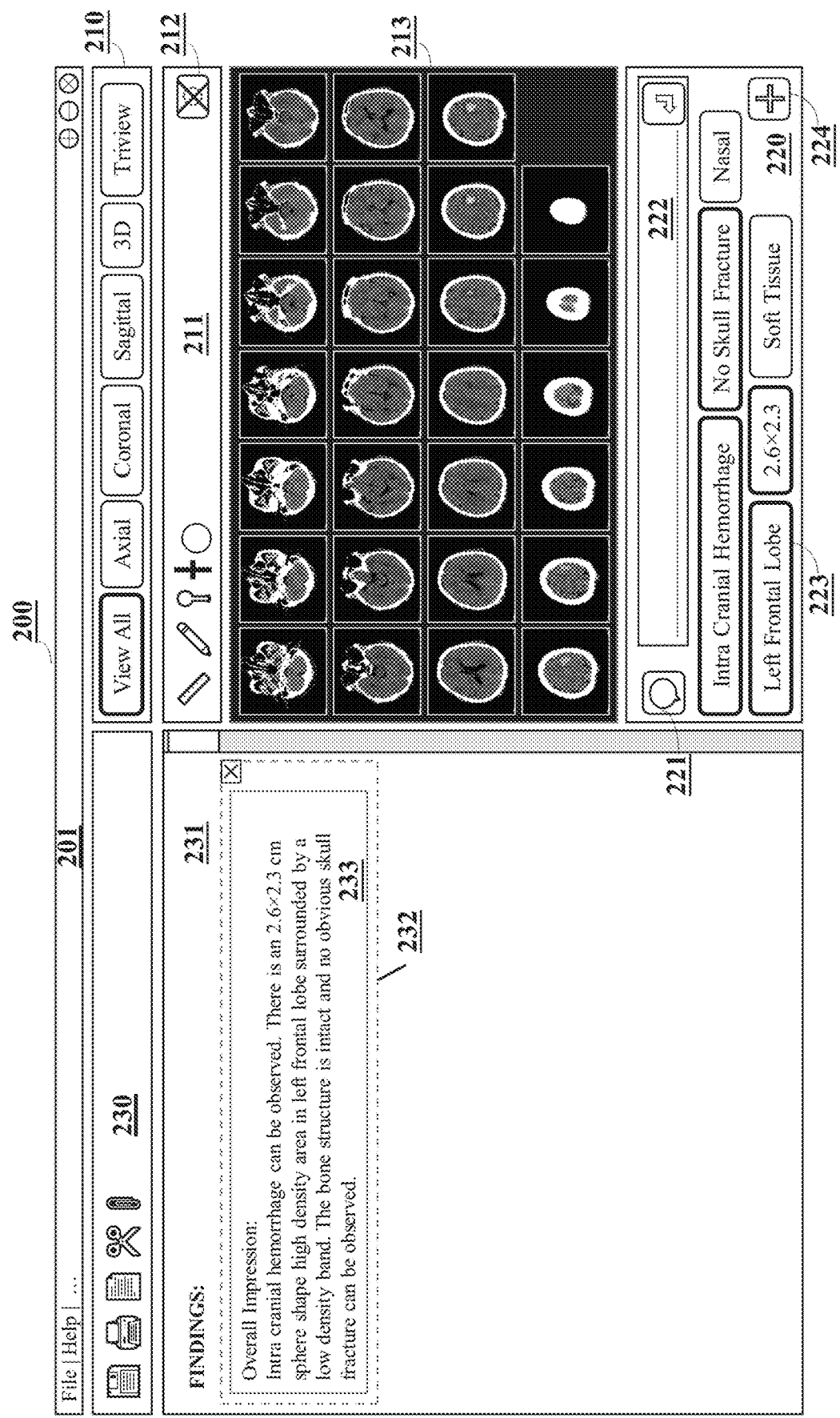
FIGS. 2A-2D illustrate exemplary user interfaces of the diagnosis report generating system of FIG. 1, according to embodiments of the disclosure.
Figure 2B:
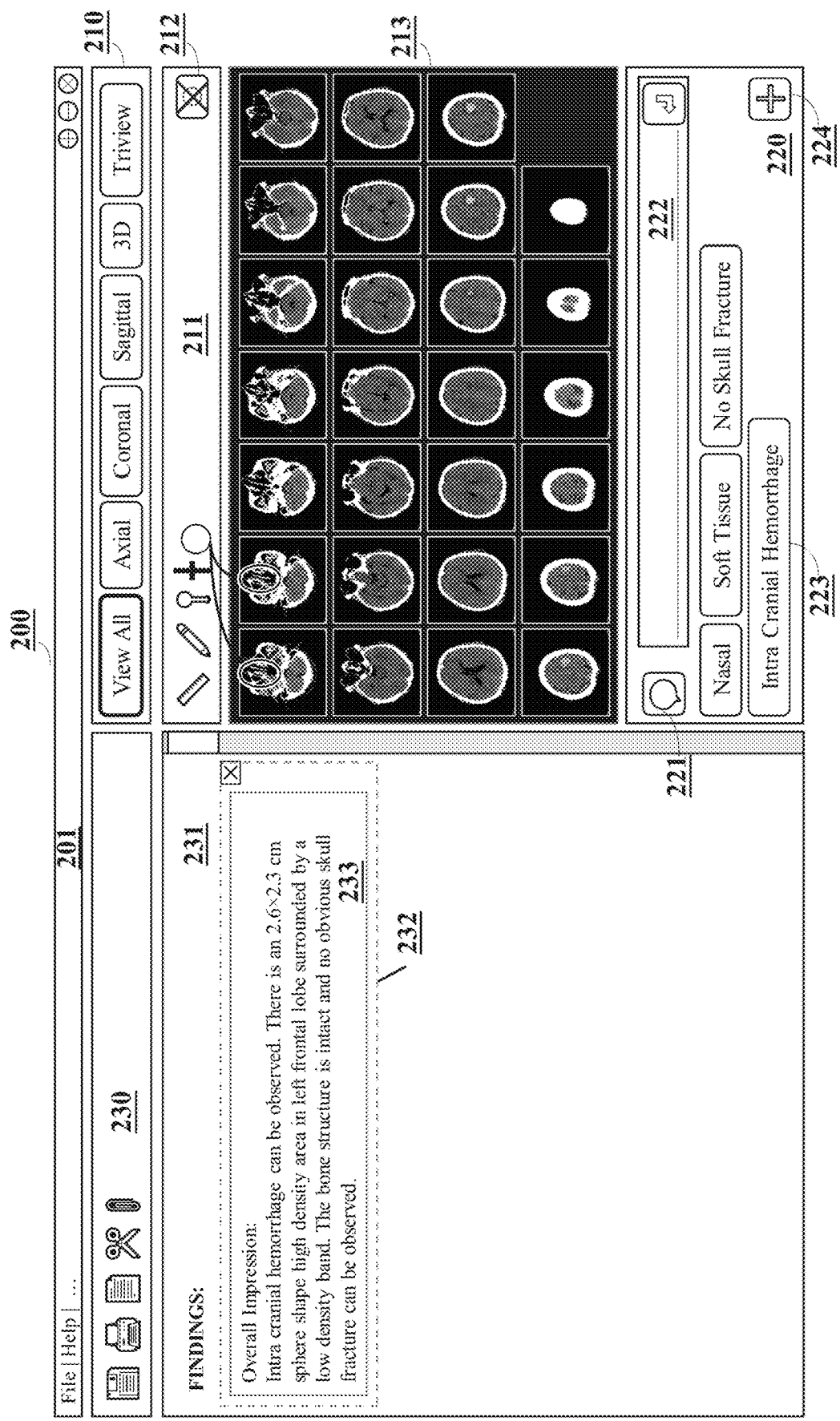
Figure 2C:
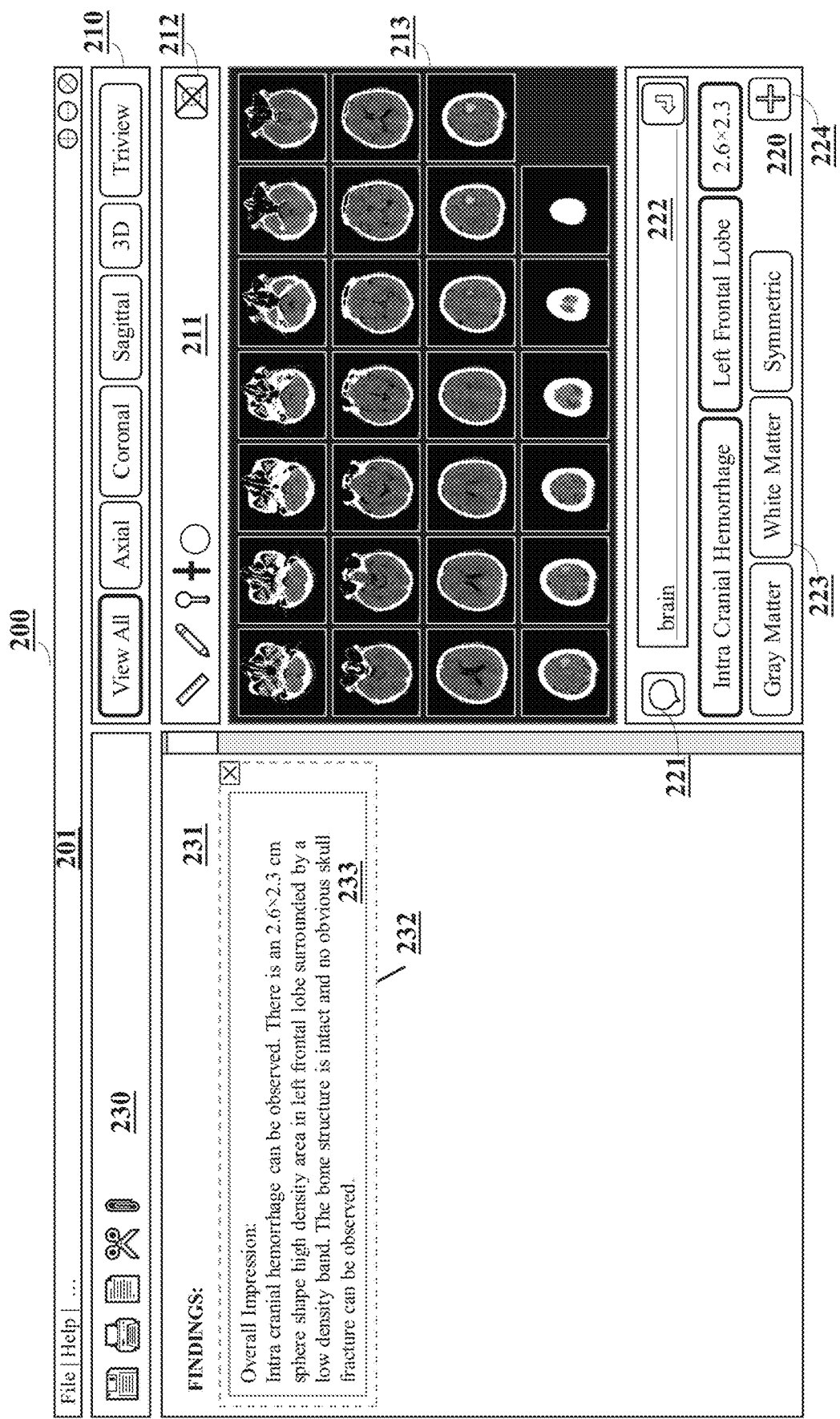
Figure 2D:
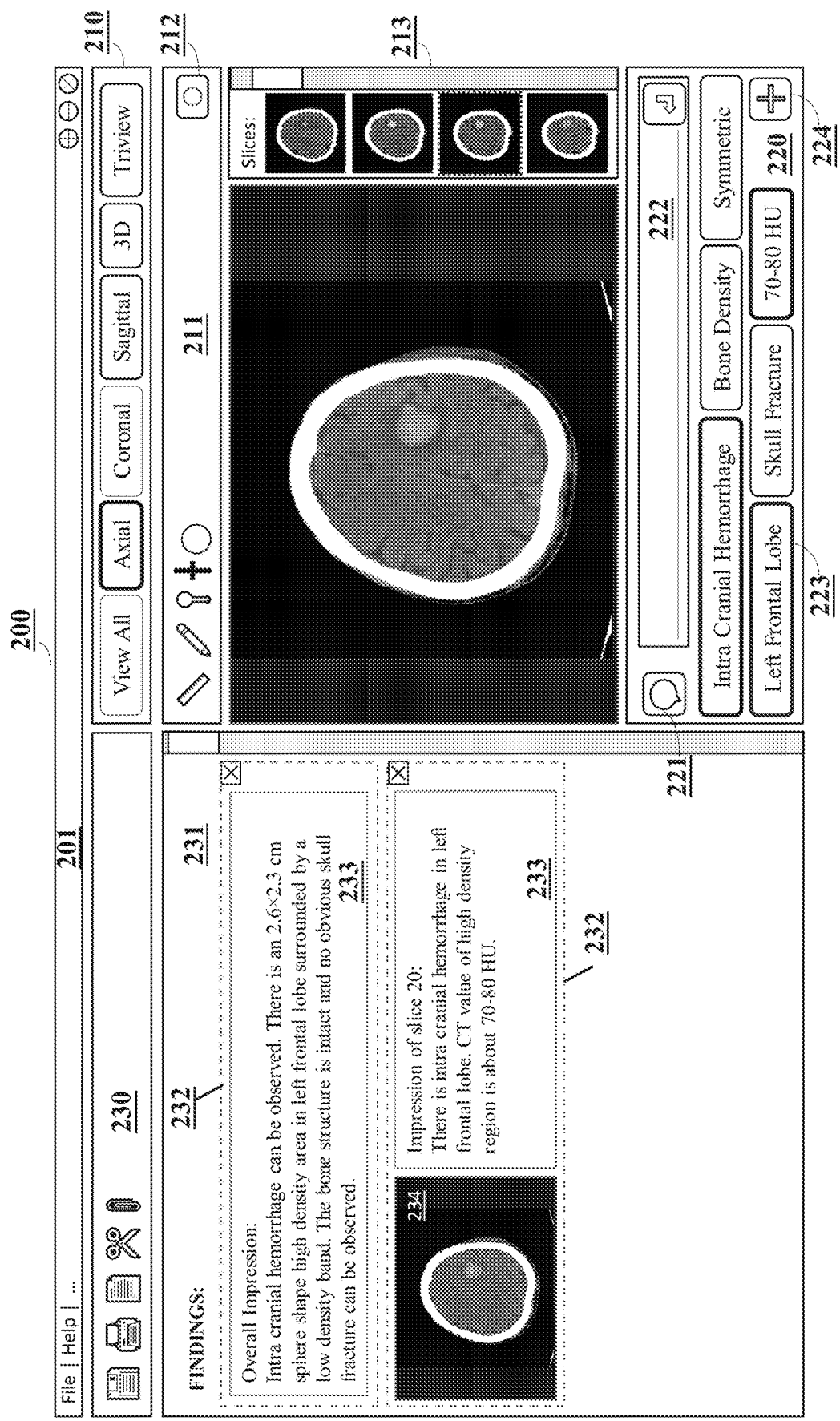

As shown in FIGS. 2A-2D, images 213 may be displayed in different views. Images 213 may be a subset of medical images 102. For 3D images, the views may include, but not limited to, a tile view, an axial view, a coronal view, a sagittal view, a 3D view, or a combination of multiple views (e.g., a triview that includes axial/coronal/sagittal views). In some embodiments, user 105 may select the desired image view from view selection bar 210, e.g., by clicking on the respective buttons. For example, user interfaces 200 in FIGS. 2A-2C show all images 213 when "view all" button is selected in view selection bar 210, and user interface 200 in FIG. 2D shows only axial images 213 as the "axial" button is selected in view selection bar 210. For different type of views, user 105 can have different interactive view operations using I/O interface 140, such as mouse clicks, keyboard operations, and touch-screen taps, etc. These operations may include, but are not limited to, zoom-in operations, zoom-out operations, shifting operations, rotation operations, panning operations, tilting operations, and image adjustment operations (e.g. image contrast adjustment operations).

User 105 may interact with the report generation process through user input area 220. For example, keywords may be selected from natural language descriptions of images 213 in the selected view. The keywords of these descriptions may be shown in keywords display area 223. In some embodiments, the keywords may be sorted according to certain rules (e.g. importance, frequency). In some embodiments, only the top keywords (e.g., in terms of importance, frequency of appearance, etc.) may be shown if the space is limited. User 105 may add corresponding natural language descriptions to diagnosis report 231 by clicking the keywords within keywords display area 223. User 105 can also choose to add all the automatically generated descriptions into the report by clicking on an "add all" button 224. In some embodiments, as shown in FIGS. 2A-2C, generated diagnosis report 231 may include various text interfaces 232 each including a message box 233 that shows the automatically generated descriptions.

In some embodiments, user interface 200 may provide image editing toolbar 211 including, e.g., drawing tools, to allow the user to interactively annotate images 213. For example, as shown in FIG. 2B, user 105 may select a drawing tool from image editing toolbar 211 and apply the tool on one or more images 213. The annotation options may include, but not limited to, drawing a circle, drawing a square, drawing a line, drawing a curve, drawing a ruler, dropping a pin point, and drawing a mask. In some embodiments, the annotation may indicate a region of interest (ROI) in an image 213. Based on the annotation and the image being viewed, processor 120 may automatically adjust and generate new descriptions and the corresponding keywords. For example, when user 105 draws circles around the ROIs in images 213, as shown in FIG. 2B, keywords display area 223 may be updated with keywords associated with the selected ROIs. In some embodiments, the order of the keywords may also be adjusted accordingly. For example, because the selected ROIs correspond to the nasal area that contains mostly soft tissue, the keywords "nasal" and "soft tissue" may be listed first in keywords display area 223.

In some embodiments, user 105 may use voice input to generate description by clicking a speak button 221. Speech content may be received by I/O interface 140, e.g., a microphone, after speak button 221 is clicked. Based on the speech content and the image viewed, processor 120 may automatically adjust and generate new descriptions and the corresponding keywords. The order of the keywords may also be adjusted accordingly. In some embodiments, processor 120 may also detect whether the speech content is a complete description of the viewed image. If the speech content is a complete description of the image, the text of speech content may be automatically transcribed and added to the report as part of the description.

In some embodiments, user 105 may type text in a message box 222. The text entered can be keywords, phrases, or sentences. For example, user 105 may enter "brain" in message box 222, as shown in FIG. 2C. Based on the entered text and the image viewed, processor 120 may automatically adjust and generate new descriptions and the corresponding keywords. The order of the keywords may also be adjusted accordingly. For example, because "brain" is entered as shown in FIG. 2C, the keywords associated with brain, such as "left frontal lobe," "gray matter," "white matter," etc. are ranked higher as compared to those in FIG. 2A.

In some embodiments, user 105 can edit diagnosis report 231 by editing message box 233, as shown in FIG. 2A-2C. For example, the user may edit the description of "overall impression" in message box 233 by deleting, adding, or modifying the description, e.g., using a keyboard or a touch-screen. User 105 may also edit the content of message boxes 233 using report edit toolbar 230. In some embodiments, diagnosis report 231 may further include image views. For example, as shown in FIG. 2D, a screenshot 234 of the current view (e.g., axial view) can be added to diagnosis report 231. In some embodiments, this feature can be turned on or off by a switch 212. As shown in FIG. 2D, another message box 233 may also be added to display automatically generated impression of the corresponding slice shown in screenshot 234. In some embodiments, for the same image or the same set of images observed, the descriptions and the screenshots may be grouped in a block and the user may delete the block when necessary.

Returning to FIG. 1, memory 150 and storage 160 may include any appropriate type of mass storage provided to store any type of information that processor 120 may need to operate. Memory 150 and/or storage 160 may be a volatile or non-volatile, magnetic, semiconductor-based, tape-based, optical, removable, non-removable, or other type of storage device or tangible (i.e., non-transitory) computer-readable medium including, but not limited to, a ROM, a flash memory, a dynamic RAM, and a static RAM. Memory 150 and/or storage 160 may be configured to store one or more computer programs that may be executed by processor 120 to perform functions disclosed herein. For example, memory 150 and/or storage 160 may be configured to store program(s) that may be executed by processor 120 for image processing and diagnosis report generation.

Memory 150 and/or storage 160 may be further configured to store information and data used by processor 120. For instance, memory 150 and/or storage 160 may be configured to store medical images 102 acquired by image acquisition system 101, patient information, and user input data, e.g., speech content, received by I/O interface 140. Memory 150 and/or storage 160 may also store image processing results generated by image processing unit 122, as well as intermediary data created during image processing. Memory 150 and/or storage 160 may also store various parts of a diagnosis report generated by deep-learning diagnosis report unit 124, such as images, tables, and texts, etc. The various types of data may be stored permanently, removed periodically, or discarded immediately after each frame of data is processed.

Figure 3:
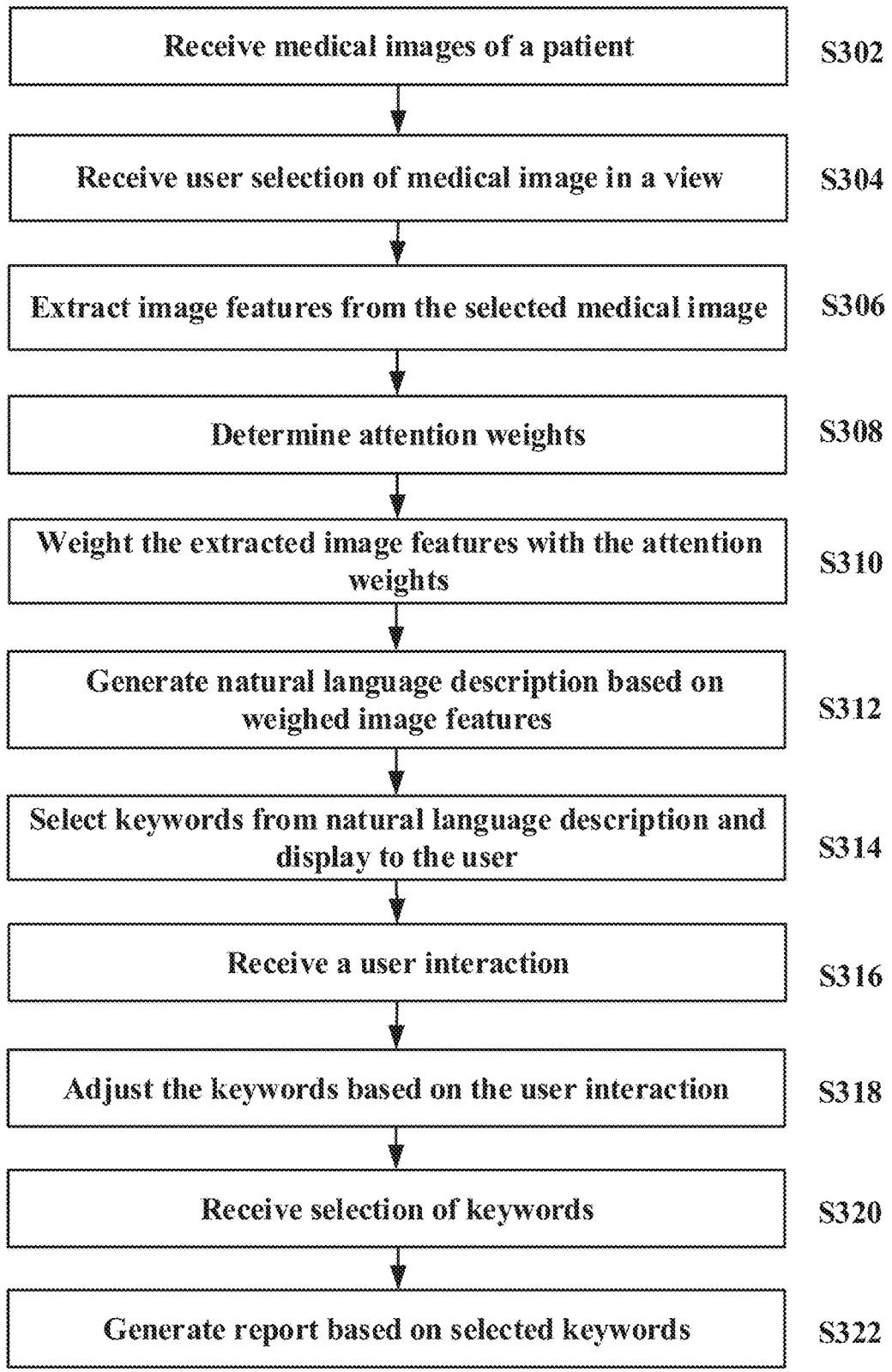
FIG. 3 shows a flow chart of an exemplary method for generating a diagnosis report, according to embodiments of the disclosure.

FIG. 3 shows a flow chart of an exemplary method 300 for generating a diagnosis report, according to embodiments of the disclosure. For example, method 300 may be implemented by diagnosis report generating device 100 shown in FIG. 1. However, method 300 is not limited to that exemplary embodiment. Method 300 may include steps S302-S322 as described below. It is to be appreciated that some of the steps may be optional to perform the disclosure provided herein. Further, some of the steps may be performed simultaneously, or in a different order than shown in FIG. 3.

In step S302, diagnostic report generating system 100 may receive one or more medical images 102 associated with a patient, e.g., from image acquisition device 101 or a medical image database. Medical images 102 may be 2D or 3D images. Medical images 102 can be generated from any imaging modality, such as functional MRI (e.g., fMRI, DCE-MRI and diffusion MRI), Cone Beam CT (CBCT), Spiral CT, Positron Emission Tomography (PET), Single-Photon Emission Computed Tomography (SPECT), X-ray, optical tomography, fluorescence imaging, ultrasound imaging, and radiotherapy portal imaging, etc., or the combination thereof. In some embodiments, medical images 102 may be generated using contrast agent to enhance the image contrast. In some embodiments, diagnostic report generating system 100 may pre-process medical images 102. In some embodiments, the preprocessing may include resizing, normalization, filtering, contrast balancing, etc.

In step S304, diagnostic report generating system 100 may receive a user selection of one or more images 213 in a view. For example, the views may include, but not limited to, a tile view, an axial view, a coronal view, a sagittal view, a 3D view, or a combination of multiple views (e.g., a triview). In some embodiments, user 105 may select the desired image view from view selection bar 210 as shown in FIGS. 2A-2D, e.g., by clicking on the respective buttons.

In step S306, diagnostic report generating system 100 may extract image features from the selected image(s) 213. In some embodiments, a CNN is implemented in step S306 to extract image features. In step S308, diagnostic report generating system 100 may determine attention weights. In some embodiments, attention weights may be implemented as numerical values used to quantify the contribution of each image feature of the image in the decision of outputting a specific word in the generated report. For example, an attention weight of a higher value indicates that the corresponding image feature is more important. In step S310, the extracted image features may be weighted with the respective attention weights. The weighted image features may reflect the respective levels of importance.

In step S312, diagnostic report generating system 100 may generate a natural language description of selected image(s) 213 based on the weighted image features. In some embodiments, an RNN may be implemented to generate the natural language description. In step S314, diagnostic report generating system 100 may further select keywords from the natural language description and provide the keywords to user for selection. For example, the keywords may be displayed in keywords display area 223 of FIG. 2A-2D to user 105. In some embodiments, the keywords may be ranked based on their relevance to the selected image and displayed according to their respective rankings. If the RNN returns a long list of keywords, the first N keywords in the ranked list may be displayed.

In step S316, diagnostic report generating system 100 may receive a user interaction. In some embodiments, the user interaction may be provided through I/O interface 140. As one example, user 105 may select a ROI or otherwise annotate currently viewed image(s) 213. For instance, user 105 may select a drawing tool from image editing toolbar 211 and apply the tool on one or more images 213 to draw the ROI, as shown in FIG. 2B. As another example, user 105 can choose to use voice input to generate a description by clicking speak button 221, and speak to a microphone to provide speech content. As another example, user 105 can type a word, a phrase, or a sentence using a keyword or a touch-screen. For instance, user 105 may enter "brain" in message box 222, as shown in FIG. 2C.

In step S318, diagnostic report generating system 100 may adjust the natural language description and the keywords based on the user interaction. For example, diagnostic report generating system 100 may update the description and keywords by performing steps S306-S314 based on the selected ROI, the speech content transcribed from user's voice input, or the text input typed in by the user. In some embodiments, the order of the keywords may also be adjusted accordingly.

In step S320, diagnostic report generating system 100 may receive the user's selection of keywords. For example, user 105 may click on the keywords displayed in keywords display area 223 to select one or more keywords that he/she would like to include in diagnosis report 231. In step S322, diagnostic report generating system 100 may generate the diagnosis report based on the selected keywords. In some embodiments, the natural language description corresponding to the user selected keywords included in the report may be generated based on the user selected keywords. For example, as shown in FIG. 2A, user 105 may select keywords "intra cranial hemorrhage," "no skull fracture," "left frontal lobe," and "2.6×2.3." Accordingly, the description corresponding to these keywords may be added to message box 233 of diagnosis report 231, i.e., "Intra cranial hemorrhage can be observed" as corresponding to keyword "intra cranial hemorrhage," "There is an 2.6×2.3 cm sphere shape high density area in left frontal lobe surrounded by a low density band" as corresponding to keywords "left frontal lobe" and "2.6×2.3," and "The bone structure is intact and no obvious skull fracture can be observed" as corresponding to keyword "no skull fracture." The generated report, e.g., diagnosis report 231, may be displayed in user interface 200 on display 130.

Figure 4:
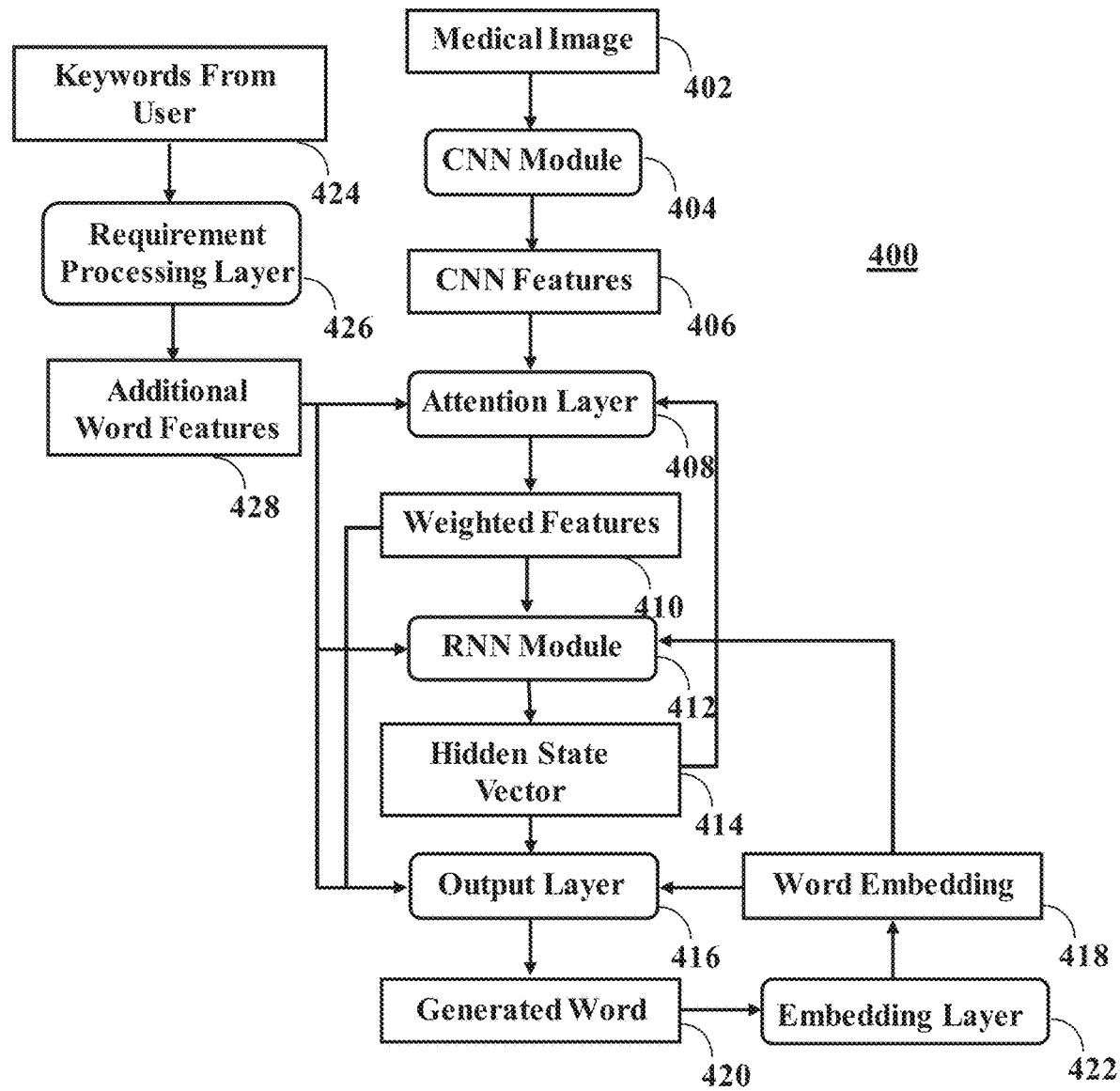
FIG. 4 shows a data flow diagram for an exemplary deep learning diagnosis report generation process, according to embodiments of the disclosure.

FIG. 4 shows an exemplary end-to-end diagnosis report generation model 400, according to embodiments of the disclosure. For example, end-to-end diagnosis report generation model 400 may be used by deep learning diagnosis report unit 124 of diagnosis report generating device 100 in FIG. 1. In some embodiments, model 400 may be implemented to perform steps S306-S312 of method 300 in FIG. 3. Model 400 may include learning networks and layers 402-428 as described below. However, it is to be appreciated that model 400 is not limited to the exemplary embodiment shown in FIG. 4.

In some embodiments, end-to-end diagnosis report generation model 400 may take one or more pre-processed images, e.g., a medical image 402, as input and output the description of the medical image (e.g., a text-based description) together with attention weights for the input image(s). In some embodiments, medical image 402 may be an image view or an ROI of an image selected by the user. In some embodiments, when the input includes multiple images, all the images may be input into model 400 as a whole (concatenated) and processed at the same time.

As shown in FIG. 4, in some embodiments, end-to-end diagnosis report generation model 400 may include a combination of a CNN module 404 for extracting CNN features 406 from medical image 402, an RNN module 412 for modeling the report, and an attention layer 408 as a connection between CNN features 406 and the generated report. In some embodiments, CNN module 404 is configured to extract image features from medical image 402. For example, CNN module 404 can include a VGG16/19 CNN network, a Densenet CNN network, or other types of suitable CNN networks.

In some embodiments, attention layer 408 may be constructed by weight matrices that assign different weights to the image features in different regions of medical image 402. CNN features 406 may be weighted by the attention weights generated by attention layer 408 and become weighted features 410. Weighted features 410 emphasize certain regions in the image to guide the generation of words (e.g., a subsequent word in a sequence) in the report. In some embodiments, attention layer 408 may take CNN features 406, a hidden state vector 414 generated by RNN module 412 in a previous iteration as inputs, as well as additional word features 428 if necessary.

In some embodiments, additional word features 428 may be used for guiding the generated report based on keywords 424 selected/added by a user, e.g., using user interaction area 220 of FIGS. 2A-2D, where the user can choose one or more keywords from those automatically generated by system 100, or add other keywords. In some embodiments, additional word features 428 may be generated by a requirement processing layer 426 based on keywords 424 selected/added by the user. In some embodiments, requirement processing layer 426 may be implemented by a multiple-layer RNN, e.g., a Long Short-Term Memory (LSTM) or a Gated Recurrent Unit (GRU). In some embodiments, additional word features 428 may embed the keyword requirements and may be utilized as an input to attention layer 408, RNN module 412, and output layer 416 to guide the word-generating process to match the requirements.

In some embodiments, RNN module 412 may use weighted features 410, word embedding 418 of the generated word in the previous iteration as input and generate hidden state vector 414. In some embodiments, RNN module 412 may additionally take additional word features 428 as an input if necessary. In some embodiments, RNN module 412 may be constructed by repeating a Long Short-Term Memory (LSTM) or Gated Recurrent Unit (GRU) recursively.

In some embodiments, output layer 416 may select a word from the vocabulary at each time point, based on hidden state vector 414. In some embodiments, output layer 416 can be constructed as a fully-connected layer. Words may be continuously generated/sampled from the vocabulary until a stop token is sampled, which encodes the end of a report. In some embodiments, generated word 420 by output layer 416 may be used to create word embedding 418 by embedding layer 422.

In some embodiments, end-to-end diagnosis report generation model 400 may be trained using sample medical images and their corresponding diagnosis reports (e.g., text-based descriptions) provided by radiologists/clinicians (serving as ground truths). For languages that don't have natural word boundaries, such as character-based languages (e.g., Chinese and Japanese), word segmentation may be performed on the reports before feeding the segmented words into the network for training.

In some embodiments, the model may be trained end-to-end using a loss function that combines the assessment of the errors from CNN module 404 and RNN module 412. In some embodiments, the loss function can be defined by Equation (1):

$$\text{loss}_{total} = \lambda_{CNN} \ell_{CNN} + \lambda_{RNN} \ell_{RNN} \quad (1)$$

where $\ell_{CNN}$ is a suitable loss for medical image-related task in the CNN part (for example, cross-entropy loss for classification task and root mean squared error for regression task), $\ell_{RNN}$ is a suitable loss for word correctness in the RNN part (typically cross-entropy loss), $\lambda_{CNN}$ and $\lambda_{RNN}$ are regularization parameters that controls the contributions of the CNN and RNN losses in the total loss, to balance the different magnitudes of the CNN loss and the RNN loss. In some embodiments, a gradient descent method may be applied to optimize the loss function to determine the optimal set of values for the model parameters.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor-based, tape-based, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It will be apparent to those skilled in the art that various modifications and variations can be made to the disclosed system and related methods. Other embodiments will be apparent to those skilled in the art from consideration of the specification and practice of the disclosed system and related methods.

It is intended that the specification and examples be considered as exemplary only, with a true scope being indicated by the following claims and their equivalents.

What is claimed is:

1. A system for generating a report based on a medical image of a patient, comprising:
    a communication interface configured to receive the medical image acquired by an image acquisition device; and
    at least one processor, configured to:
        generate a natural language description of the medical image as a direct output of a learning network applied to the medical image, wherein the learning network is configured to extract image features from the medical image, assign weighs to the image features, and generate the natural language description of the medical image based on the extracted image features and the assigned weights;
        automatically determine keywords from the natural language description of the medical image;
        generate the report describing the medical image of the patient based on the keywords; and
        provide the report for display.

2. The system of claim 1, wherein the learning network comprises a convolutional neural network and a recursive neural network connected in series, wherein the convolutional neural network is configured to extract the image features from the medical image and the recursive neural network is configured to generate the natural language description of the medical image.

3. The system of claim 2, wherein the learning network further comprises an attention layer in between the convolutional neural network and the recursive neural network, wherein the attention layer is configured to assign the weights to the image features, wherein the recursive neural network is configured to generate the natural language description of the medical image based on the extracted image features respectively weighted by the weights.

4. The system of claim 2, wherein the convolutional neural network comprises a VGG16/19 CNN network or a Densenet CNN network.

5. The system of claim 2, wherein the recursive neural network comprises at least one of a long short-term memory (LSTM) or a gate recurrent unit (GRU).

6. The system of claim 1, wherein to generate the report based on the keywords, the at least one processor is further configured to:
    receive a keyword selection among the keywords; and
    generate the report based on the keyword selection.

7. The system of claim 6, wherein the keyword selection is made by a user through a voice input, an annotation, or a text input.

8. The system of claim 1, wherein the at least one processor is further configured to:
    receive a selection of a region of interest in the medical image; and
    automatically update the report to describe the selected region of interest based on the learning network.

9. The system of claim 1, wherein the at least one processor is further configured to:
    receive a selection of a view of the medical image; and
    automatically update the report to describe the selected view based on the learning network.

10. The system of claim 1, further comprising a display configured to display the report with the medical image, wherein the display includes a touchscreen configured to receive a user interaction with the medical image.

11. A method for generating a report based on a medical image of a patient, comprising:
    receiving the medical image; by a communication interface, wherein the medical image is acquired by an image acquisition device;
    generating, by at least one processor, a natural language description of the medical image as a direct output of a learning network applied to the medical image, wherein the learning network is configured to extract image features from the medical image, assign weighs to the image features, and generate the natural language description of the medical image based on the extracted image features and the assigned weights;
    automatically determining, by the at least one processor, keywords from the natural language description of the medical image;
    generating the report, by the at least one processor, describing the medical image of the patient based on the keywords; and
    providing the report for display.

12. The method of claim 11, wherein the learning network comprises a convolutional neural network and a recursive neural network connected in series, wherein the convolutional neural network is configured to extract the image features from the medical image and the recursive neural network is configured to generate the natural language description of the medical image.

13. The method of claim 12, wherein the convolutional neural network comprises a VGG16/19 CNN network or a Densenet CNN network.

14. The method of claim 12, wherein the recursive neural network comprises at least one of a long short-term memory (LSTM) or a gate recurrent unit (GRU).

15. The method of claim 12, wherein the learning network further comprises an attention layer in between the convolutional neural network and the recursive neural network, wherein the attention layer is configured to assign the weights to the image features, wherein the recursive neural network is configured to generate the natural language description of the medical image based on the extracted image features respectively weighted by the weights.

16. The method of claim 11, wherein generating the report based on the keywords further comprising:
   receiving a keyword selection among the keywords, wherein the keyword selection is made by a user through a voice input, an annotation, or a text input; and
   generating the report based on the keyword selection.

17. The method of claim 11, further comprising:
   receiving a selection of a region of interest in the medical image; and
   automatically updating the report to describe the selected region of interest based on the learning network.

18. The method of claim 11, further comprising:
   receiving a selection of a view of the medical image; and
   automatically update the report to describe the selected view based on the learning network.

19. A non-transitory computer-readable medium having a computer program stored thereon, wherein the computer program, when executed by at least one processor, performs a method for generating a report based on a medical image of a patient, comprising:
   receiving the medical image acquired by an image acquisition device;
   generating a natural language description of the medical image as a direct output of a learning network applied to the medical image, wherein the learning network is configured to extract image features from the medical image assign weighs to the image features, and generate the natural language description of the medical image based on the extracted image features and the assigned weights;
   automatically determining keywords from the natural language description of the medical image;
   generating the report describing the medical image of the patient based on the keywords; and
   providing the report for display.

20. The non-transitory computer-readable medium of claim 19, wherein the learning network comprises a convolutional neural network and a recursive neural network connected in series, wherein the convolutional neural network is configured to extract the image features from the medical image and the recursive neural network is configured to generate the natural language description of the medical image.

* * * * *